Figure 1:
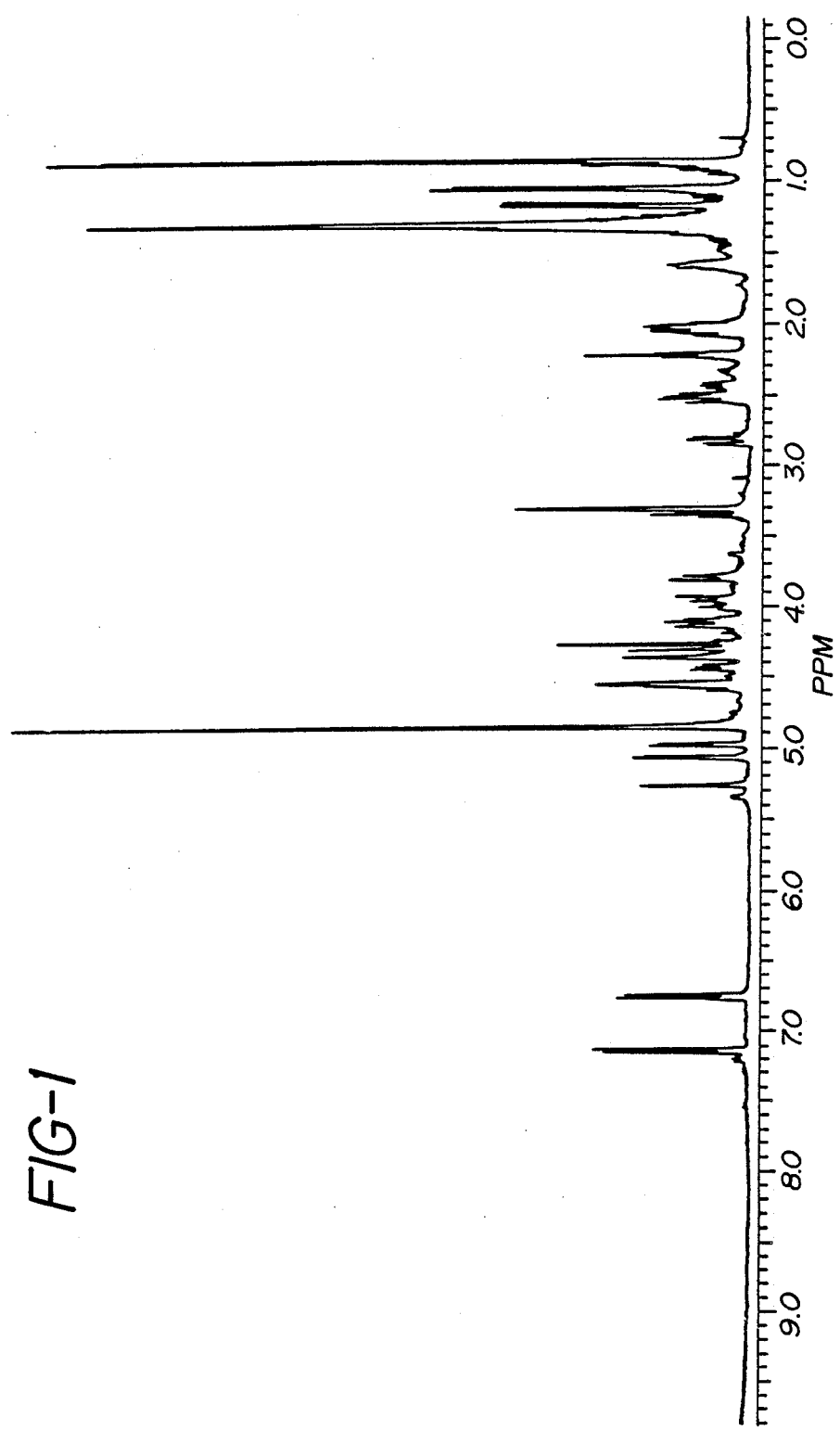

United States Patent [19]

Giacobbe et al.

[11] Patent Number: 4,968,608

[45] Date of Patent: Nov. 6, 1990

[54] PROCESS FOR ANTIFUNGAL FERMENTATION PRODUCT

[75] Inventors: Robert A. Giacobbe, Lavallette, N.J.; Sagrario M. Del Val, Madrid, Spain; Richard L. Monaghan, Somerset; Robert E. Schwartz, Westfield, both of N.J.

[73] Assignee: Merck & Co., Inc., Rahway, N.J.

[21] Appl. No.: 105,797

[22] Filed: Oct. 7, 1987

[51] Int. Cl.$^5$ .......................... C12P 1/02; C12N 1/00; C12N 1/38; C12N 1/14

[52] U.S. Cl. ..................................... 435/71; 435/171; 435/243; 435/244; 435/254; 435/911; 530/317

[58] Field of Search ............. 435/71, 171, 243, 253.6, 435/244, 254, 911; 530/317

[56] References Cited

U.S. PATENT DOCUMENTS

| | | |
|---|---|---|
| 3,978,210 | 8/1976 | Mizuno et al. |
| 4,024,245 | 5/1977 | Higgens et al. |
| 4,024,246 | 5/1977 | Hoehn et al. |
| 4,173,629 | 11/1979 | Dreyfuss et al. ................... 424/118 |
| 4,287,120 | 9/1981 | Abbott et al. |
| 4,288,549 | 9/1981 | Boeck et al. |
| 4,293,485 | 10/1981 | Debono ................................. 435/71 |
| 4,293,487 | 10/1981 | Debono |
| 4,320,053 | 3/1982 | Abbott et al. |
| 4,320,054 | 3/1982 | Abbott et al. |
| 4,322,338 | 3/1982 | Abbott et al. |

FOREIGN PATENT DOCUMENTS 57549 10/1977 Belgium.
3050385A 2/1980 United Kingdom.

OTHER PUBLICATIONS

Porter 1975 Cultural Conditions for Antibiotic-Producing Microorganisms. Methods Enzymol. XLIII, 3-23.
Fantini 1975 Strain Development, Methods Enzymol, XLIII, 25-41.
Benz, et al., Helv. Chim. Acta 57, 8, 2459-2477 (1974).
Traber et al., Helv. Chim. Acta 62, 4, 1252-1267 (1979).
Roy et al., J. Antibiotics, XL, 3, 275-280 (1987).
Mukhopadhyay et al., J. Antibiotics XL 3, 281-289 (1987).
Gordee et al., J. Antibiotics XXXVII, 9, 1054-1065 (1984).

Primary Examiner—Charles F. Warren
Assistant Examiner—Christopher S. F. Low
Attorney, Agent, or Firm—Alice O. Robertson; Charles M. Caruso

[57] ABSTRACT

An antifungal agent produced by cultivation of *Zalerion arboricola* is a cyclic lipopeptide with very high activity against human pathogens and of very low mammalian toxicity. Its production and isolation are also described.

10 Claims, 1 Drawing Sheet

PROCESS FOR ANTIFUNGAL FERMENTATION PRODUCT

The present invention is concerned with a compound produced by fermentation on cultivation of a microorganism of as yet unclassified species of fungus, and particularly with a method of producing and isolating the compound therefrom. The compound and the use of the compound for the control of fungi, particularly in the treatment of human mycotic infections is claimed in copending application Ser. No. 105,795 filed contemporaneously herewith.

DESCRIPTION OF THE INVENTION

According to the present invention it has been discovered that a new substance produced by an initially unidentified microorganism which was isolated from water, now identified as *Zalerion arboricola*, has very useful antifungal activities. The compound has broad spectrum antifungal activity, particularly against fungal pathogens infecting human beings such as *Candida albicans, Candida parapsilosis* and other *Candida* species. The substance is a lipopeptide of very low toxicity, rendering it especially adaptable for therapeutic applications as hereinafter detailed.

The novel active agent is a white solid which may be characterized by the following physical properties:

a decomposition temperature of 206°–214° C.;

an empirical formula of $C_{51}H_{82}N_8O_{17}$ determined by high resolution FAB (Fast Atom Bombardment mass spectrometric measurement, calculated for $C_{51}H_{82}N_8O_{17} + Li = 1085.5958$, found = 1085.6146);

an amino acid composition as determined by gas chromatogram/mass spectra of the trimethylsilyl derivative of the total acid hydrolysates of one equivalent each of threonine, hydroxyproline, methylhydroxyproline, and hydroxyglutamic acid.

$^1$H NMR Spectra in CD$_3$OD at 400 MHz as seen in FIG. 1; and $^{13}$C NMR chemical shifts obtained in CD$_3$OD at 100 MHz as follows: 11.20, 11.64, 19.75, 20.25, 20.78, 27.00, 28.07, 30.33, 30.37, 30.61, 30.76. 31.19, 31.29, 32.94, 34.83, 36.69, 38.10, 38.54, 39.07, 39.53, 45.93, 51.39, 53.01, 55.59, 56.31, 57.11, 58.35, 62.43, 68.18, 70.08, 70.55, 70.61, 71.26, 73.94, 75.72, 75.84, 76.86, 116.06(x2), 129.43(x2), 132.86, 158.22, 168.80, 172.16, 172.35, 172.40, 173.12, 174.24, 175.47, 176.88 ppm.

The substance having such property is a compound which based on spectral data and other physical properties is believed may be represented by Formula I.

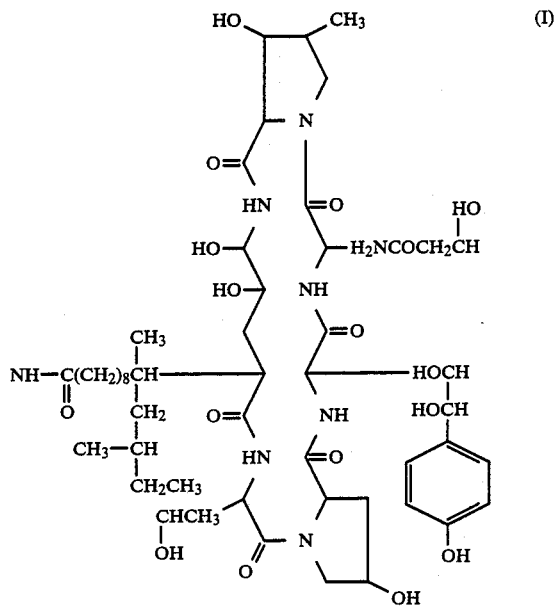

The compound may be identified, using the Chemical Abstracts system of nomenclature, as 1-[(4R, 5R) 4,5-dihydroxy-N$^2$-(10,12-dimethyl-1-oxotetradecyl)-L-ornithine]-5-(threo-3-hydroxy-L-glutamine)echinocandin B. For convenience, the compound hereinafter shall be referred to as Compound I.

The compound is soluble in a variety of organic solvents such as methanol, ethanol, dimethylformamide, dimethyl sulfoxide, ethyl acetate and the like.

The compound of this invention has useful antifungal activities adapted to be employed for the control of various fungi, both filamentous fungi and yeasts. It is particularly useful against those causing pathogenic mycotic infections, such as *Candida albicans, Candida parapsilosis* and the like, where not only high activity has been noted but consistently high activity over an expanded panel of strains of the organisms.

Although a number of antibiotics and other antifungal agents are known to be active against *Candida albicans* and certain other fungal pathogens, their utility as a therapeutic agent is oftentimes limited. For example, amphotericin B, an effective antifungal antibiotic, is generally limited to those situations in which the patient has a progressive potentially fatal fungal infection in which the possible life-saving benefit of the drug must be balanced against the untoward and dangerous side effects. The antifungal agent of the present invention is not only a very effective antifungal agent but is substantially non toxic and substantially free of undesirable side reactions.

One of the shortcomings of a number of drugs is the rather narrow differential between the effective dose and the concentration of drug which causes a detrimental side reaction in the patient. One harmful and potentially fatal side reaction is red blood cell lysis. Compounds which show this property at concentrations approaching the effective dose have limited applicability. Compound I has been found unexpectedly not only to be very effective as an antifungal agent, but further has been found to require a concentration of drug far above that anticipated for any therapeutic use before red blood cell lysis occurs.

Additionally, Compound I has been found to significantly prolong the survival of mice infected with *Candida albicans* and also to eradicate *Candida albicans* from kidneys of experimentally infected mice. These properties point to a new antifungal drug with great potential in the therapy of human mycotic infections.

In addition to the unexpected properties which renders Compound I useful as a therapeutic agent in the treatment of mycotic infections, the broad antifungal spectrum exhibited by this antibiotic renders it useful as an active component wherever control of fungi is desired. Thus, the compound may be employed to control the growth of fungal species which may be found on or in cosmetics, leather, electrical insulation, textiles, paints and other materials such as *Aspergillus, Penicillium, Alternaria, Monilia, Aureobasidium;* to control the growth of fungi which infect plants, plant parts and plant products such as *Erysiphe polygoni, Alternaria solani,* and *Cochliobolus miyabeanus;* to control fungi which infect soil such as *Rhizoctonia solani, Fusarium solani* and *Pythium ultimum;* fungi which infect wood, pulp and paper such as *Lenzites trabea* and *Ceratocystis pilifera.*

Some other of the specific filamentous fungi and yeasts which may be controlled include Aspergillus species: *A. niger, A. flavus, A. fumigatus, A. oryzae, A. awalmari, A. versicolor, A. sydowi, A. nidulans,* and *A. terreus;* or *Penicillium* species: *P. notatum, P. rogueforti, P. chrysogenum, P. oxalicum, P. spinulosum, P. martensii, P. citrinum, P. digitatum, P. expansion, P. italcium, P. cyclopium,* and *P. funiculosum; Neurospora sitophila; Phoma terrestris; Rhizomucor miehei; Alternaria solani, Chaetomium globosum; Trichoderma harzianum; Fusarium oxysporum; Ustilago maydis, Ceratocystis ulmi; Verticillium serrae; Botrytis allii; Candida* species such as *C. albicans, C. tropicalis, C. rugosa, C. guilliermondii, C. pseudotropicalis,* and *Torulopsis glabrata.*

The antifungal agent of the present invention, Compound I, is conveniently produced by cultivating a strain of microorganism designated MF 5171 in the culture collection of Merck & Co., Rahway, N.J. and recovering said agent from the culture medium. A sample of the culture capable of producing the compounds has been deposited under the Budapest Treaty in the Culture Collection of the American Type Culture Collection at 12301 Parklawn Drive, Rockville, MD 20852. The sample has been assigned the accession number ATCC 20868.

The colonial and morphological description of ATCC 20868 ar set forth below:

A. Morphological description

Globose, approximately 6.0 microns in diameter, thick-walled, dark colored structures similar to chlamydospores develop along mycelium and often appear to be intercalary. These structures appear to divide, forming multi-celled groups of 4–8 cells which do not break up readily. On some media, strands of mycelia cluster together, forming rope-like structures and the multicelled groups form large clusters as if held together by mucilaginous material.

B. Colonial description

1. Czapek Dox agar

Colonies are slow growing, growth not extensive, flat with irregular edges. Mycelium is black, shiny; surface becomes dull, granular appearing, black to greenish brown as colony ages.

2. Corn agar

Colonies are slow-growing. Growth is not extensive. Mycelium is black, shiny surface becoming powdery, dull black as colony ages.

3. Potato dextrose agar, Sabouraud maltose agar and yeast extract malt extract dextrose agar Colonies are slow growing. Growth is not extensive, is slightly raised in the center, radiately furrowed irregular edges except on Sabouraud maltose agar where the edges are hyaline and regular. Mycelium is black, shiny; becomes dull powder, black as colony ages.

Although the invention is discussed hereinbelow principally with respect to the specific strain, it is well-known in the art that the properties of microorganisms may be varied naturally and artificially. Thus, all strains of the genus ATCC 20868 including varieties and mutants, whether obtained by natural selection, produced by the action of mutating agents such as ionizing radiation or ultraviolet irradiation, or by the action of chemical mutagens such as nitrosoguanidine, are contemplated to be within the scope of this invention.

Compound I may be produced in a form adaptable for drug use by cultivating the strain ATCC 20868 in a nutrient medium until a substantial amount of antibiotic activity is detected in the culture medium and thereafter recovering the active component from the fermentation medium in a suitable solvent, concentrating the solution of active component then and subjecting the concentrated material to chromatographic separation.

The fermentation is carried out in a medium containing sources of carbon and nitrogen assimilable by the microorganisms and generally low levels of inorganic salts. In addition, the medium may be supplemented with trace metals, although if complex sources of carbon and nitrogen are employed, they are usually present in the complex sources.

The sources of carbon include glycerol, sugars, starches and other carbohydrates or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 5 percent by weight of the medium is satisfactory. These carbon sources can be used individually or several such carbon sources may be combined in the same medium.

The sources of nitrogen include amino acids such as glycine, arginine, threonine, methionine and the like as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 90 percent by weight of the medium.

Among the nutrient inorganic salts, which can be incorporated in the culture medium are the customary salts capable of yielding sodium, potassium, magnesium, ammonium, calcium, phosphate, sulfate, chloride, carbonate, and like ions. Also included are trace metals such as cobalt, manganese, iron, molybdenum, zinc, cadmium, and the like.

The medium suitable for carrying out the fermentation may be solid or liquid.

Solid media may have a millet, corn, oats, soy bean or wheat base. One medium having a millet base is Medium 2 in Example I. Other representative solid media include the following:

| Media | Weight or Volume Per 250 ml Flask |
|---|---|
| Medium A | |
| Corn (cracked) | 10.0 g |
| Yeast extract | 0.5 g |
| Sodium tartrate | 0.1 g |
| Monosodium glutamate | 0.1 g |
| Corn oil | 0.1 ml |
| Ferrous sulfate | 0.01 g |
| Water | 15-20 ml |
| Medium B | |
| Millet | 15 g |
| Yeast extract | 0.5 g |
| Sodium tartrate | 0.1 g |
| Ferric sulfate.7H$_2$O | 0.01 g |
| Sucrose | 0.5 g |
| Alfalfa | 0.5 g |
| Corn oil | 0.1 ml |
| Water | 15 ml |
| Medium C | |
| Millet | 15 g |
| Yeast extract | 0.5 g |
| Sodium tartrate | 0.1 g |
| Ferric sulfate.7H$_2$O | 0.01 g |
| Silica gel | 0.5 g |
| Alfalfa | 0.5 g |
| Monosodium glutamate | 0.1 g |
| Corn oil | 0.1 ml |
| Water | 15 ml |
| Medium D | |
| Millet | 15 g |
| Yeast extract | 0.5 g |
| Sodium tartrate | 0.1 g |
| Ferric sulfate.7H$_2$O | 0.01 g |

In addition, media may be prepared by substituting wheat, barley, oats or soy bean for the millet or corn above.

Liquid media also may be employed. Fermentation on a larger scale is generally more conveniently carried out employing a liquid medium. It has been found that although conventional liquid media may be employed to obtain Compound I, such media have not been found to be suitable for obtaining good yields of the desired antibiotic. However, by incorporating from about 6 to 9 percent by weight of glycerol, it has been found that good yields of the desired antibiotic compound may be obtained. Thus, methods and compositions for producing Compound I in liquid medium constitute an aspect of the process of the present invention. A preferred liquid medium is one described in Example III. Other more conventional liquid media such as the following, or a modification thereof also may be employed:

| Medium | |
|---|---|
| Dextrose | 10 g |
| Glycerol | 10 ml |
| Soy Flour | 4 g |
| Peptonized milk | 4 g |
| Tomato paste | 4 g |
| Lard water | 4 g |
| Potassium dihydrogen phosphate | 2 g |
| Cobalt chloride hexahydrate | 0.01 g |
| Distilled Water | 1000 ml |
| pH 7 | |

For producing the compounds of the present invention, a fermentation medium containing ATCC 20868 is prepared by inoculating spores or mycelia of the antibiotic-producing organism into a suitable medium and then cultivating under aerobic conditions.

The procedure generally is first to inoculate a preserved source of culture from an agar slant containing nutrient medium into a nutrient seed-producing medium and to obtain, preferably through a two step procedure, growth of the organisms which serve as seeds in the production of the antifungal agent.

In this process, a slant section of a preserved culture of ATCC 20868 is inoculated into an appropriate liquid nutrient seed medium of pH in the range 5 to 8.1, optimally 6 to 7.5, and the flasks incubated with or without agitation at temperatures in the range of from about 15° C. to about 30° C., preferably 20° to 28° C. Agitation when employed, may be up to 400 rpm, preferably, about 200 to 220 rpm. The incubation is carried out over a period of from 2 to 30 days, preferably 2 to 14 days. When growth is abundant, usually between 2 and 4 days, the culture growth may be used to inoculate the production medium for the production of the antifungal agent. Preferably however, a second stage fermentation is carried out, inoculating with a portion of the culture growth and then employing similar conditions but generally with a shortened incubation period of about 1 to 2 days. The growth then is employed to inoculate the production medium.

The fermentation production medium inoculated with the culture growth is incubated for 3 to 30 days, usually 7 to 14 days with or without agitation. The fermentation may be conducted aerobically at temperatures ranging from about 20° C. to about 40° C. For optimum results, it is most convenient to conduct these fermentations at a temperature in the range of from about 24° C. to about 30° C. Temperatures of about 24°-28° C. are most preferred. The pH of the nutrient medium suitable for producing the instant compounds can vary from about 5.0 to 8.5 with a preferred range of from about 6.0 to 7.5. After the appropriate period for the production of the desired compound or compounds, the latter is recovered from the fermentation medium as hereinafter more fully described.

The active material may be recovered from the fermentation medium by steps comprising
(1) adding alcohol to said medium, stirring and filtering to recover the active component in the resulting aqueous alcoholic solution;
(2) concentrating the aqueous alcoholic solution to a small volume of primarily aqueous solution;
(3) intimately contacting the resulting concentrated alcoholic aqueous solution with a water immiscible oxygenated organic solvent or an aromatic or halogenated hydrocarbon solvent to extract or partition the active component thereinto and concentrating;
(4) subjecting the material recovered in Step (3) to at least one chromatographic separation, wherein in each chromatographic separation, the active component from the eluates exhibiting activity against *Candida albicans* are combined and concentrated to recover Compound I.

The exact steps may vary somewhat depending on whether the fermentation had been carried out in liquid or solid medium, what solvent is employed and what adsorbent or combination of adsorbents is employed.

When the fermentation is carried out in solid medium, the first step may be carried out by adding an alcoholic solvent to the fermentation medium, thoroughly mixing, then filtering, recovering and concentrating the aqueous alcohol filtrate. Preferably, the concentrated filtrate is first back-extracted or washed with a lower aliphatic hydrocarbon solvent such as hexane or other alkane to remove alkane soluble impurities. The alkane washed filtrate may be extracted or partitioned with a water-immiscible oxygenated organic solvent or an aromatic or halogenated hydrocarbon solvent, and the resulting solution concentrated, then loaded onto a column for at least one, generally several chromatographic separation steps. Alternatively, the water-immiscible solvent partition or extract may be concentrated and coated or coated while concentrating onto silica gel, and the coated gel loaded onto a silica gel column for chromatographic separation.

When the fermentation is carried out in a liquid medium, the mycelial solids are filtered and recovered from the fermentation medium. Alcohol is added to the mycelial cake, and the mycelial solid thoroughly mixed with the alcohol, filtered, and the filtrate collected and concentrated. Then in a manner similar to that described for isolation from solid media, the alcoholic aqueous solution is intimately admixed with a water-immiscible oxygenated organic solvent or an aromatic or halogenated hydrocarbon solvent to extract or partition the product thereinto, and the resulting solution then employed in chromatographic separation.

The alcoholic solvent to be employed in the initial extraction of the active agent from the solid nutrient medium or from the mycelial pad may be any of the lower alcohols such as methanol, ethanol, isopropanol, and the like. Methanol is preferred.

The water-immiscible non-polar organic solvent useful for extracting or partitioning the active agent from the methanol solution are esters, such as ethyl acetate, isopropyl acetate, butyl acetate and the like and ketones, such as methyl ethyl ketone. However, halohydrocarbons such as methylene chloride and aromatic hydrocarbons such as benzene or toluene may be employed. Lower aliphatic esters are preferred.

The chromatographic separation may be carried out by employing conventional column chromatography with non-ionic resin or by high performance liquid chromatography employing reverse phase resin. The fractions containing the antibiotic Compound I may be detected by bioautography using *Candida albicans*. Generally, more than one chromatographic separation steps are employed. In a most preferred procedure, one or more separations are carried out employing column chromatography and a final separation is carried out employing high performance liquid chromatography (HPLC) with $C_{18}$ reverse phase resin.

When conventional column chromatography is employed for chromatographic separations, silica gel is the preferred adsorbent. Usually more than one chromatographic separation is required. Silica gel may be used in all the separations while employing different eluting agents. However, it may be combined advantageously with the use of a different adsorbent such as a dextran adsorbent sold under the trade name of SEPHADEX LH-20 (Pharmacia). Other adsorbents such as alumina, styrene-divinylbenzene copolymers available commercially as DIAION HP-20, HP-30, HP-40 (Mitsubishi Chemical Industries, Ltd.) and AMBERLITE XAD-2, XAD-4, XAD-16 (Rohm and Haas Co.) also may be employed.

In the fractionation and recovery of the active component by chromatography on silica gel, ester/alcohol mixtures with increasing concentration of alcohol provide good separations. A mixture of ethyl acetate and methanol has been found to be especially useful. These may be employed in isocratic, step gradient or continuous gradient systems. When a dextran adsorbent such as SEPHADEX LH-20, is employed, a chlorohydrocarbon/hydrocarbon/alcohol solvent system may be employed. A mixture of methylene chloride/hexane/methanol has been found to be especially useful.

In carrying out the HPLC separation, the alcohol solution containing material recovered from the conventional chromatography is concentrated and the residue dissolved in methanol and loaded on a column packed with commercial reverse phase resin or on a column filled with silica gel/$C_{18}$ reverse phase resin prepared as amply reported in the literature. The column then is operated using acetonitrile/water (1:1 or optionally other ratios) at 800–2000 psi which produces a flow rate of about 20 ml/min. Separation is monitored at 210 nm.

The product is recovered from any of the chromatographic procedures by combining the *Candida albicans* active fractions and concentrating under reduced pressure.

The superior potential of antibiotic Compound I of the present invention as a therapeutic agent in the treatment of mycotic infections rests not only with the antifungal activity but with freedom from red blood cell lysis at therapeutic concentrations and substantial absence of any form of toxicity. The efficacy against fungi, particularly human pathogens, may be illustrated with the results of tests against *Candida albicans, Candida parapsilosis* and certain other *Candida* species.

The activity may be seen in an agar dilution assay employing a yeast nitrogen base dextrose agar medium. In carrying out the assay, Compound I was solubilized in 10 percent dimethyl sulfoxide (DMSO) supplemented with one drop of Tween 20. Twofold dilutions were made with sterile distilled water/10 percent DMSO to obtain final drug concentrations in the agar dilution assay plates ranging from 128 to 0.06 $\mu$g/ml.

The yeast cultures, maintained in yeast maltose (YM) broth, were transferred to fresh YM medium and incubated overnight at 35° C. with shaking (250 rpm). After incubation, each culture was diluted in sterile saline to yield a final concentration of $3 \times 10^5$ to $3 \times 10^6$ colony forming units (CFU)/ml.

Each prepared plate was inoculated using a Denley Multipoint Inoculator (Denley, Sussex, England) which delivers approximately 0.001 milliliter to the agar surface resulting in inoculation of from $3 \times 10^2$ to $3 \times 10^3$ CFUs. The plates were incubated at 28° C. for 48 hours. The minimum inhibitory concentrations (MICs) were recorded as the lowest concentrations of drug showing no growth or less than three CFU/spot.

Useful antimycotic properties may be illustrated with the results demonstrating the superior effectiveness of Compound I against various Candida species as seen in the following table:

| Fungus | Strain no | Minimum Inhibitory Concentration (mg/ml) Compound I |
|---|---|---|
| *Candida albicans* | MY1058 | 0.25 |
| *C. albicans* | MY1055 | 0.50 |

-continued

| Fungus | Strain no | Minimum Inhibitory Concentration (mg/ml) Compound I |
|---|---|---|
| C. albicans | MY0992 | 0.50 |
| C. albicans | MY1013 | <0.06 |
| C. albicans | MY1029 | *>128.0 |
| C. parapsilosis | MY1009 | 8.0 |
| C. parapsilosis | MY1010 | 8.0 |
| C. tropicalis | MY1011 | 0.25 |
| C. tropicalis | MY1012 | 128.0 |
| C. pseudotropicalis | MY1040 | 1.0 |
| C. krusei | MY1020 | 2.0 |
| C. stellatoidea | MY1017 | 0.25 |
| C. rugosa | MY1022 | 32.0 |

*Substantially reduced growth was observed; possible media interference with activity.

In a similar assay, Compound I was tested against an expanded panel of 34 different strains of *Candida albicans* and 13 different strains of *Candida parapsilosis*. In the case of *Candida albicans*, it was found that against 28 of the strains, the MIC was in the range 0.063 to 0.25 ug/ml and only against 5 strains was it greater than 1 ug/ml. In the case of *Candida parapsilosis*, it was found that against 12 of the 13 strains the MIC was in the range of 2.0 to 8.

The foregoing results are merely exemplary of the superior and consistent antimycotic properties shown by Compound I. As seen subsequently, the compound is a broad spectrum antibiotic effective against many fungal species including other human pathogens.

The property of Compound I of requiring concentration of drug far above the therapeutic dose levels to effect red blood cell lysis was discovered in a standard titration/hemolysis assay using fresh blood drawn from CD-1 female mice. Concentration of drug in the range of from 0.39 to 400 µg/ml in 5 percent dextrose and a drug free control were employed.

In carrying out the determination, the assay tubes prepared by mixing together 2 milliliters of appropriate drug dilution and 0.5 milliliter of red blood cell suspension were gently shaken to mix the contents and then the tubes were incubated at 25° C. for two hours. At the end of this time, the tubes were examined visually for complete or partial red blood cell hemolysis and compared to a drug free control. The minimum lytic concentration (MLC) was taken as the highest drug concentration that did not lyse the red blood cells. The MLC for Compound I was 400 µg/ml. The same experiment carried out with amphotericin B showed the MLC for amphotericin B to be 12.5 µg/ml.

From the various test results, it is determined that for therapeutic use generally from about 1.4 to about 2.8 mg/kg of body weight of the antibiotic may be employed while considering the patient's health, weight, age and other factors which influence response to a drug. These amounts, when expressed as doses suitable for human beings, are in the range of from about 100 mg to about 200 mg daily by oral or parenteral administration.

The outstanding properties are most effectively utilized when the compound is formulated into novel pharmaceutical compositions with a pharmaceutically acceptable carrier according to conventional pharmaceutical compounding techniques.

The novel compositions contain at least 1% by weight of the active compound. In preparing the compositions, Compound I is intimately admixed with any of the usual pharmaceutical media.

The compositions are preferably prepared in oral dosage form. For liquid preparations, the antifungal agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form for ease of administration and uniformity of dosage.

The antifungal agent is formulated in antifungal compositions for injection and may be presented in unit dosage form in ampoules or in multidose containers, if necessary with an added preservative. The compositions may also take such forms as suspensions, solutions or emulsions in oily or aqueous vehicles such as 0.85 or percent sodium chloride or 5 percent dextrose in water, and may contain formulating agents such as suspending, stabilizing and/or dispersing agents. Buffering agents as well as additives such as saline or glucose may be added to make the solutions isotonic. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of each of the component drugs.

If the application is to be topical, the drug may be formulated in conventional creams and ointments such as white petrolatum, anhydrous lanolin, cetyl alcohol, cold cream, glyceryl monostearate, rose water and the like. Usually a 1 to 2 percent cream or solution is prepared and applied to the area to be treated.

Compound I also exhibits broad spectrum antifungal activity. This may be seen in an antifungal assay employing a disc diffusion method against yeasts and filamentous fungi (molds).

In the disc diffusion method, seeded assay plates are first prepared in one of the following manners according to the type of organism.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

Inocula for yeasts are prepared from overnight broth cultures then diluted into potato dextrose agar to a final concentration of either 40 percent or 70 percent transmission at 660 nm.

For three strains of *Candida albicans* and one strain of *Saccharomyces cerevisiae*, sterile saline is employed in place of potato dextrose broth. Assay plates are prepared by diluting the inoculum into appropriate molten agar medium, cooled to 45° C. to obtain a final concentration of 4 percent (volume/volume).

The seeded agar media thus prepared are dispensed into petri dishes for assays (11 milliliters per dish).

The samples to be tested for production of antifungal agent are applied to 6.2 mm. filter paper discs (25 microliter/disc) and air dried at 24° C. When the sample to be tested is a crude broth, it may be centrifuged prior to application. The discs bearing the material to be tested are then applied employing sterile conditions to the seeded assay plates and the samples rewet with 25 percent sterile aqueous dimethylsulfoxide (25 μl/disc). The assay plates are then incubated at either 28° C. or 37° C. for 24 hours. Following incubation, the inhibition zones are measured and recorded.

It was found that good antifungal properties were seen against filamentous fungi *Cochliobolus miyabeanus, Penicillium* sp. (three strains), *Aspergillus niger, Trichoderma* sp., *Trichoderma lignorum, Alternaria solani, Verticillium serrae, Botrytis allii, Scopulariopsis communis, Cephalosporium* sp., *Cercospora beticola, Rhizomucor miehei, Aspergillus flavus* and *Aspergillus fumigatus;* and against the yeasts *Saccharomyces cerevisiae, Candida albicans, Candida rugosa, Brettanomyces bruxellensis, Torulospora hansenii, Candida guilliermondii, Candida pseudotropicalis, Torulopsis glabrata,* and *Kluyveromyces fragilis.*

In view of the broad spectrum of activity, the antibiotic of the present invention is adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in inanimate objects.

Compositions for therapeutic applications may be prepared as previously described.

For non medical application, the product of the present invention, either singly or as a mixture may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

In practicing the invention, an antifungal amount of the compositions may be applied directly to areas where fungal control is desired.

The following examples illustrate the invention but are not to be construed as limiting:

EXAMPLE I

FERMENTATION

A frozen culture in glycerol of Isolate 2 of Culture 8525-307P originally isolated from water, identifiable as ATCC 20868, and maintained in the Merck culture collection was employed in the fermentation.

A 2 milliliter portion of the frozen culture was defrosted and aseptically transferred to a 250 milliliter unbaffled Erlenmeyer flask containing 54 milliliters of Medium 1. Medium 1, after inoculation, was incubated at 28° C. with rotary agitation (220 rpm, 2″ throw shaker) for three days. At the end of this period, 2.0 milliliters of the growth medium were aseptically transferred to each of several unbaffled 250 milliliter Erlenmeyer flasks containing Medium 1. The inoculated flasks were incubated at 28° C. for 2 days.

12.5 milliliters of the mature seed broth were inoculated into five production flasks containing Medium 2, and incubated at 25° C. for seven days under static conditions to obtain an antibiotic compound in the fermentation medium.

The media employed in the foregoing fermentation were:

| MEDIUM 1 (KF Seed Medium) | |
|---|---|
| Corn Steep Liquor | 5 g |
| Tomato Paste | 40 g |
| Oat Flour | 10 g |
| Glucose | 10 g |
| Trace Elements Mix | 10 ml |
| Distilled Water | 1000 ml |
| pH 6.8 | |
| Trace Elements Mix: | |
| $FeSO_4.7H_2O$ | 1 g |
| $MnSO_4.4H_2O$ | 1 g |
| $CuCl_2.2H_2O$ | 25 mg |
| $CaCl_2$ | 100 mg |
| $H_3BO_3$ | 56 mg |
| $(NH_4)_6MoO_2.4H_2O$ | 19 mg |
| $ZnSO_4.7H_2O$ | 200 mg |
| Distilled Water | 1000 ml |
| MEDIUM 2 (F204 Solid Medium) | |
| | Amount/flask |
| Millet Base | 15 g |
| Yeast Extract | .5 g |
| Sodium tartrate | .1 g |
| Ferrous Sulfate Crystals | .01 g |
| Monosodium Glutamic Acid | .1 g |
| Corn Oil | .1 ml |

ISOLATION

Five hundred milliliters of methanol were added to each of the five 2 liter flasks of solid phase fermentation. The contents of the flask were then combined and stirred to extract methanol soluble material and the mixture then filtered. The spent cake was stirred with an additional 2500 milliliters of methanol to further extract methanol soluble material and the mixture then filtered.

The filtrate and wash were combined and concentrated to 500 milliliters.

The aqueous methanolic concentrate thus obtained then was extracted with two 500 milliliter portions of ethyl acetate. The spent aqueous solution was loaded onto DIAION HP-20 column to adsorb the active material thereon and the latter then eluted therefrom with methanol. The eluates were combined with the previously obtained ethyl acetate extracts and the combined ethyl acetate solutions were concentrated to dryness. The residue was chromatographed on 200 milliliters of SEPHADEX LH-20 using 5:5:2 methylene chloride/hexane/methanol as eluant.

The fractions active as determined by *Candida albicans* were combined and chromatographed on 200 milliliters of silica gel (EM Science, KIESELGEL 60, 230 400 mesh) using a step gradient elution with ethyl acetate/methanol. The active fractions from this chromatography were combined, concentrated and chromatographed on silica gel using a 75:25 ethyl acetate/methanol isocratic system.

The active portions from this chromatography were then combined and placed on 100 milliliters of Sephadex LH-20 using methanol as eluting solvent. The eluate, after vaporization of the solvent, yielded 95 milligrams of a purified compound. The compound was a white solid having a $^1$H NMR spectrum as seen in FIG. 1.

EXAMPLE II

FERMENTATION

In a manner similar to that described in Example I, the contents of one frozen vial of ATCC 20868 from the Merck culture collection were defrosted and aseptically transferred to a 250 milliliter unbaffled flask containing 54 milliliters of KF medium (Medium 1) containing 0.4 percent agar. The modified Medium 1, after inoculation, was incubated at 28° C. with 220 rpm agitation for 48 hours. At the end of this period, 10 milliliters of the growth medium was transferred to a 2 liter unbaffled flask containing 500 milliliters of KF medium containing 0.4 percent agar. After inoculation, the resulting medium was incubated for 24 hours at 28° C. with 220 rpm agitation.

Twenty 2-liter flasks each containing 120 grams of Medium 2 and 120 milliliters of a stock solution consisting of

| Yeast extract | 5 parts by weight |
| Sodium tartrate | 1 part by weight |
| Ferrous sulfate crystals | 0.1 part by weight |
| Monosodium glutamic acid | 1 part by weight |
| Corn oil | 1 part by weight | were autoclaved for 20 minutes at 122° C. and then reautoclaved with 80 milliliters of water for another 20 minutes at 122° C. The flasks were allowed to cool, then inoculated with 20 milliliters of seed medium prepared as above described, and the inoculated flasks incubated at 25° C. under static conditions for 14 days.

ISOLATION

To each of nineteen 2-liter solid fermentation flasks was added 1 liter of methanol and the contents combined, stirred and filtered. The spent cake was extracted twice with 6 liters of methanol. The aqueous methanol filtrates were then concentrated and the concentrate extracted twice with 3 liters of ethyl acetate. The ethyl acetate extracts were combined, dried and concentrated to about 100 milliliters.

The concentrate was then coated on silica gel by adding 100 milliliters of methanol and 100 milliliters of silica gel thereto, intimately contacting the components and then removing the solvent on a rotary evaporator. The dried silica gel was then applied to a column of 500 milliliters of silica gel, the column washed with ethyl acetate to remove impurities and eluted with 9:1 ethyl acetate/methanol. The eluates containing antibiotic material testing positive against *Candida albicans* were recovered and combined.

The antibiotic rich cut from the silica gel chromatography was dissolved in 200 milliliters of 10:10:1 methylene chloride/hexane/methanol and the resulting solution combined with 40 milliliters of SEPHADEX LH-20 (which previously had been prepared by soaking overnight in methanol followed by washing twice with 200 milliliters of methylene chloride/hexane/methanol). After a few minutes, the supernatant was removed by filtration and the SEPHADEX LH-20 was washed with 200 milliliters of methylene chloride/hexane/methanol and then filtered. The filtrates were found not to contain the active constituent, and were discarded. The active constituent which had partitioned into the dextran Sephadex LH-20 beads was extracted therefrom by washing twice with 200 milliliters of methanol, and these methanol washes were combined and concentrated.

The methanol concentrate was next applied to 200 milliliters of silica gel and eluted with 75:25 ethyl acetate/methanol and the eluates combined and the solvent vaporized to obtain Compound I. Compound I is a white powder having a decomposition point of 206°–214° C.

EXAMPLE III

FERMENTATION

Seed broth were prepared from ATCC 20868 in a manner similar to that described in Example I. Two milliliters of the mature seed broth were inoculated into production flasks containing 45 milliliters of Medium 3 per flask and agitated on a rotary shaker at 220 rpm for 13 days at 25° C. and 50 percent relative humidity to obtain antibiotic Compound I in the fermentation medium.

Medium 3 is of the following composition:

| MEDIUM 3 | |
| --- | --- |
| | (Grams/Liter H$_2$O) |
| Glycerol | 85 g |
| Pectin | 10 g |
| Peanut Meal | 4 g |
| Peptonized Milk | 4 g |
| Tomato Paste | 4 g |
| Corn Steep | 4 g |
| Lard Water | 4 g |
| Glycine | 2 g |
| KH$_2$PO$_4$ | 2 g |
| pH = 7.0 | |

EXAMPLE IV

ISOLATION

On completion of fermentation in a liquid medium, the medium is filtered to remove the mycelial solids. Excess methanol is added to the mycelial cake, the mycelial solids thoroughly mixed with the methanol, the mixture filtered and the filtrate then concentrated. Ethyl acetate is added to the concentrate and the material partitioned or extracted thereinto. The ethyl acetate extract is then concentrated and the concentrated solution chromatographed on a silica gel column using ethyl acetate/methanol mixtures to obtain the desired product.

What is claimed is:

1. A process for producing antibiotic Compound I represented by the formula (Formula I)

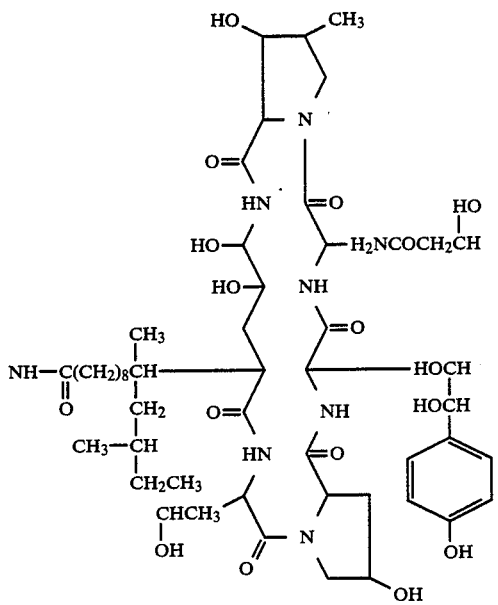

and named 1-[4R,5R)-4,5-dihydroxy-N²-(10,12-dimethyl-1-oxotetradecyl)-L-ornithine]-5-(threo-3-hydroxyl-1-glutamine)-echinocandin B by cultivating a fungus of the strain Zalerion arboricola ATCC 20868 in a liquid nutrient medium, which has incorporated therein from about 6 to about 9 percent by weight of glycerol, until a substantial amount of antifungal activity has been produced therein.

2. A process according to claim 1 wherein the cultivation is carried out aerobically in the temperature range of from about 20° C. to about 40° C., the pH in the range of from about 5.0 to 8.5 over a period of from about 3 to 30 days.

3. A process according to claim 1 which includes isolating the Compound I from the culture medium.

4. The process of claim 3 wherein the isolation is carried out by
(1) adding alcohol to said medium and stirring, then filtering to recover the active component in the resulting aqueous alcohol solution;
(2) concentrating the aqueous alcohol solution to a small volume of primarily aqueous solution;
(3) intimately contacting the resulting concentrated alcoholic aqueous solution with a water-immiscible oxygenated organic solvent or an aromatic or halogenated hydrocarbon solvent to extract or partition the active component thereinto and concentrating;
(4) subjecting the material recovered in Step (3) to at least one chromatographic separation, wherein in each chromatographic separation the active component from the eluates exhibiting activity against Candida albicans are combined and concentrated to recover Compound I.

5. A process according to claim 4 wherein in step
(1)
(a)
(i) if the culture medium is a solid medium, alcohol is added thereto.
(ii) if the culture medium is a liquid medium the mycelial solids are filtered and alcohol is added to the filter cake, (b) the alcohol and solids are thoroughly contacted, then filtered, the filter cake washed and combined with filtrate;
in step (2) the alcohol solution, after concentrating if necessary, is extracted or partitioned with a water-immiscible oxygenated organic solvent or an aromatic or halogenated hydrocarbon solvent;
in step (3)
(a) the water-immiscible organic solvent extract is loaded onto a chromatographic column
(i) directly in an organic solvent or
(ii) as adsorbent beads previously or contemporaneously coated with extracted materials;
(b) the active materials are eluted, and
in step (4) the active material is recovered by concentrating the eluant.

6. A process for producing an antifungal antibiotic compound represented by Formula I of claim 1 by cultivating a strain of Zalerion arboricola ATCC 20868 in a nutrient medium of pH of from about 5.0 to 8.5 under aerobic conditions at temperatures of from about 20° C. to 40° C. for 3 to 30 days or until a sufficient amount of the compound is produced and thereafter separating said antibiotic compound from said culture medium by (1) recovering alcohol soluble materials from the fermentation medium, (2) partitioning or extracting from the alcohol solution, material soluble in a water-immiscible oxygenated organic solvent or an aromatic or halogenated hydrocarbon solvent, (3) chromatographically separating the organic solvent-soluble active materials, and (4) then recovering the antifungal antibiotic compound.

7. A process for producing an antifungal antibiotic compound represented by Formula I of claim 1 by cultivating a strain of Zalerion arboricola ATCC 20868 in a liquid nutrient medium which has incorporated therein from about 6 to about 9 percent by weight of glycerol at a pH of from about 5.0 to 8.5 under aerobic conditions at temperatures of from about 20° to 40° C. for from 3 to 30 days and thereafter separating said antibiotic compound from said culture medium by (a) filtering off the mycelial solids and adding alcohol to the filter cake, (b) thoroughly contacting the mycelial solids and alcohol, filtering, washing the filter cake with alcohol, and combining the washings with the filtrate and concentrating, (c) extracting or partitioning the aqueous alcohol solution with a water-immiscible oxygenated hydrocarbon solvent, (d) chromatographing the organic solvent extract, (e) recovering the eluates which are active against Candida albicans, and (f) combining the eluates and vaporizing off the solvent.

8. A culture medium suitable for the production of the compound of formula I of claim 1 from the microorganism Zalerion arboricola ATCC 20868 consisting essentially of a nutrient medium of assimilable carbon, assimilable nitrogen and inorganic salts which has been modified by the addition of from about 6 to 9 percent by weight of glycerol.

9. A process for producing an antibiotic Compound I represented by the formula

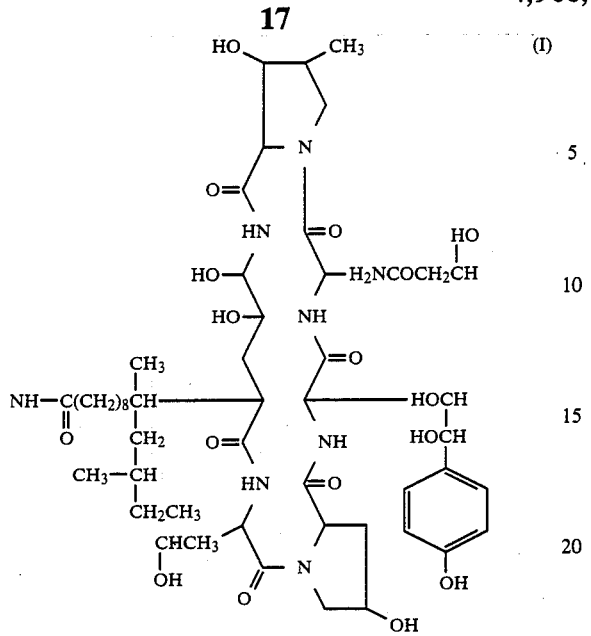

an named 1-[(4R,5R)-4,5-dihydroxy-N²-(10,12-dimethyl-1-oxotetradecyl)-L-ornithine]-5-(thero-3-hydroxy-1-glutamine) echinocandin B by cultivating a strain of fungus ATCC 20868 available from the American Type Culture Collection in a liquid nutrient medium, which has incorporated therein from about 6 to about 9 percent by weight of glycerol, until a substantial amount of antifungal activity has been produced therein.

10. A culture medium suitable for the production of the compound of formula (I) of claim 9 from microorganism ATCC 20868 consisting essentially of a nutrient medium of assimilable carbon, assimilable nitrogen and inorganic salts which has been modified by the addition of from about 6 to 9 percent by weight of glycerol.

* * * * *